United States Patent
Awad et al.

(10) Patent No.: US 9,889,170 B1
(45) Date of Patent: Feb. 13, 2018

(54) SYNTHESIS OF NANOPARTICLES USING BALANITES AEGYPTIACA

(71) Applicant: KING SAUD UNIVERSITY, Riyadh (SA)

(72) Inventors: Manal Ahmed Gasmelseed Awad, Riyadh (SA); Rabab Abd El Moneim Khalil El Dib, Giza (EG); Awatif Ahmed Hendi, Riyadh (SA); Shaza Mohamed Adel Al-Massarani, Riyadh (SA); Khalid Mustafa Osman Ortashi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/287,653

(22) Filed: Oct. 6, 2016

(51) Int. Cl.
| | |
|---|---|
| *A61K 36/185* | (2006.01) |
| *A61K 36/889* | (2006.01) |
| *A01N 65/08* | (2009.01) |
| *A01N 59/16* | (2006.01) |
| *A61K 33/24* | (2006.01) |
| *A61K 33/30* | (2006.01) |
| *A61K 9/16* | (2006.01) |
| *C12P 3/00* | (2006.01) |
| *C01G 9/02* | (2006.01) |
| *B22F 9/24* | (2006.01) |
| *B22F 1/00* | (2006.01) |

(52) U.S. Cl.
CPC ............ *A61K 36/185* (2013.01); *A01N 59/16* (2013.01); *A01N 65/08* (2013.01); *A61K 9/16* (2013.01); *A61K 33/24* (2013.01); *A61K 33/30* (2013.01); *B22F 1/0044* (2013.01); *B22F 9/24* (2013.01); *C01G 9/02* (2013.01); *C12P 3/00* (2013.01); *B22F 2009/245* (2013.01); *B22F 2301/255* (2013.01); *B22F 2998/10* (2013.01); *C01P 2004/16* (2013.01); *C01P 2004/32* (2013.01); *C01P 2004/62* (2013.01); *C01P 2004/64* (2013.01)

(58) Field of Classification Search
None
See application file for complete search history.

(56) References Cited

U.S. PATENT DOCUMENTS

| 8,057,682 B2 * | 11/2011 | Hoag | B22F 1/0018 210/688 |
|---|---|---|---|
| 2011/0110723 A1 * | 5/2011 | Varma | B22F 1/0018 405/128.75 |

OTHER PUBLICATIONS

Aktar et al. (2013) ACS Sustainable Chem. Eng. 1, 591-602.*
Ashaal et al. (2010) J. Ethnopharmacology 127: 495-501.*
Chothani et al. (2011) Pharmacogn. Rev. Jan-June: 5(9): 55-62.*
Mittal et al. (2013) Biotechnology Advances 31: 346-356.*
Noruzi (2015) Bioprocess Biosyst Eng 38: 1-14.*

* cited by examiner

*Primary Examiner* — Chris R Tate
*Assistant Examiner* — Russell Fiebig
(74) *Attorney, Agent, or Firm* — Richard C. Litman

(57) ABSTRACT

A method of preparing nanoparticles from desert date can include providing a metal salt solution comprising metal ions; providing desert date extract solution that comprises a reducing agent, and combining the metal ion solution and the desert date extract solution while stirring at a temperature in the range of 25° C. to 100° C. to produce metal or metal oxide nanoparticles. The metal nanoparticles can be gold nanoparticles. The metal oxide nanoparticles can be zinc oxide nanoparticles. The nanoparticles can be used to inhibit the growth or proliferation of a cancer cell and/or microorganisms.

2 Claims, 21 Drawing Sheets

SYNTHESIS OF NANOPARTICLES USING *BALANITES AEGYPTIACA*

BACKGROUND OF THE INVENTION

1. Field of the Invention

The present invention relates to bio-nanotechnology and particularly a green synthesis of highly stable nanoparticles using aqueous extract of *Balanites aegyptiaca* (L.) Delile fruit mesocarp as a reducing/stabilizing agent.

2. Description of the Related Art

Nanoparticles exhibit completely new or improved properties compared to their corresponding bulk materials. Because of their size, catalytic property, ability to deliver drug, increased efficacy, and decreased toxicity, nanotechnology finds applications in various fields including healthcare, defense and day-to-day life.

*Balanites aegyptiaca* is a species of tree, classified either as a member of the Zygophyllaceae or the Balanitaceae. Zygophyllaceae is a family of flowering plants, which is a wild evergreen tree grown in dry and savannah areas of Africa, the Middle East and South Asia. The fruits of the tree, *Balanites aegyptiaca* (L.) Delile, are edible and known as desert dates. *Balanites aegyptiaca* (L.) Delile is also known in Arabic as Lalob or Hegleeg. The plant has multipurpose medicinal applications. In traditional medicine, *Balanites* herb is used as complementary therapy for different diseases in the African subcontinent and other countries. Interestingly, *Balanites* herb has displayed promising performance in laboratory studies on HIV/AIDS patients. *Balanites* seed extract has been used as an anticancer agent and fruit mesocarp extract as fasciolicidal agents, which is related to their polar constituents.

Thus, a green method of producing nanoparticles utilizing *Balanites aegyptiaca* extract thereby solving the aforementioned problems is desired.

SUMMARY OF THE INVENTION

A method for preparing nanoparticles can include: providing a metal salt solution comprising metal ions; providing desert date extract solution; and combining the metal salt solution and the desert date extract solution to produce the metal/metal oxide nanoparticles. The metal salt solution can include chloroauric acid ($HAuCl_4$) when the nanoparticles to be synthesized are gold nanoparticles or zinc nitrate hexahydrate $Zn(NO_3)_2 \cdot 6H_2O$ when the nanoparticles to be synthesized are zinc oxide nanoparticles.

A method for preparing nanoparticles can include dissolving *Balanites Aegyptiaca* powder in an organic solvent to form a solution; adding the solution to boiling water under ultrasonic conditions to form a mixture; and stirring the mixture at a temperature of about 24° C. and a speed of about 2000 rpm to obtain *Balanites Aegyptiaca* nanoparticles.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
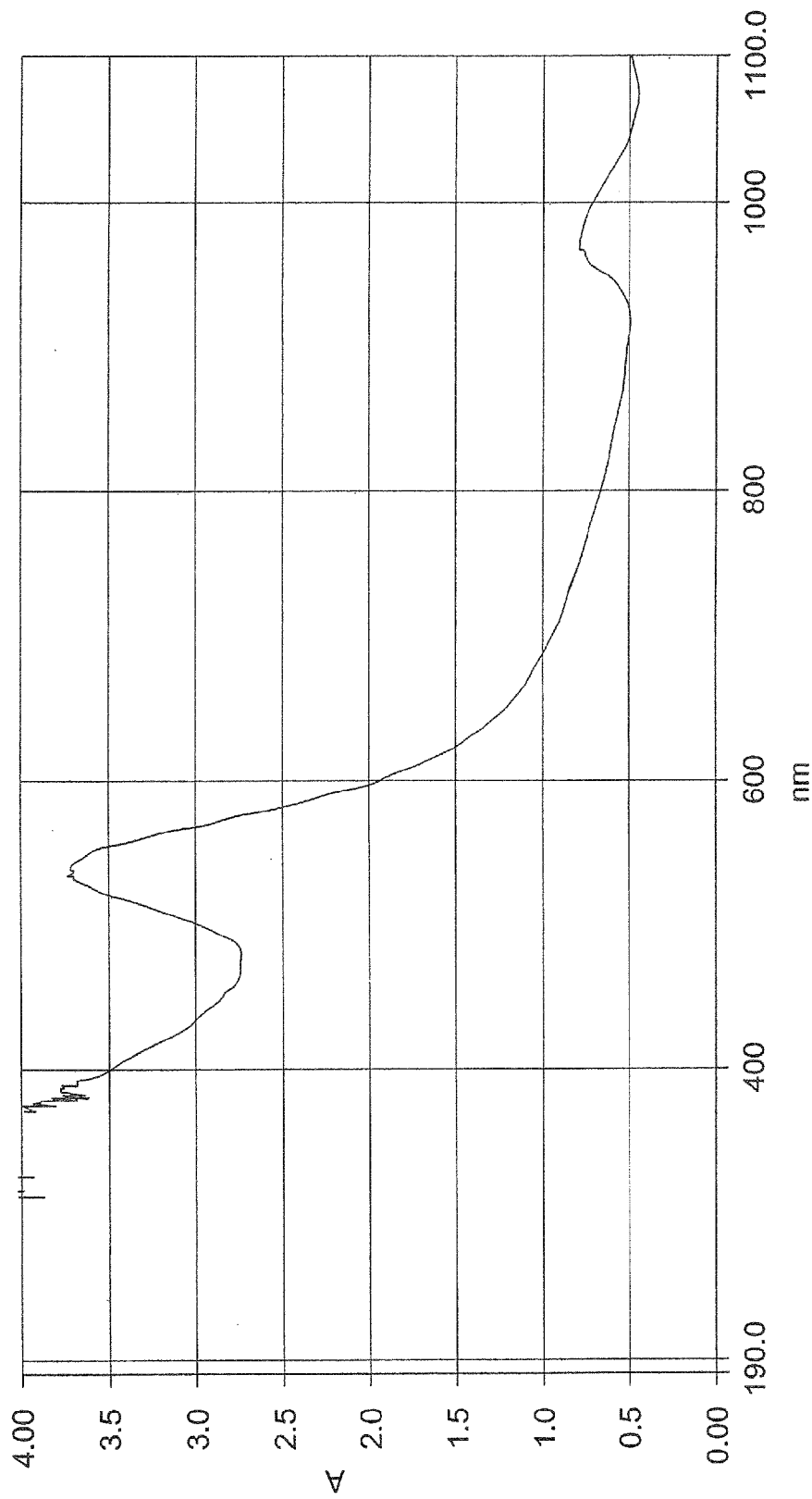
FIG. 1 shows a UV-vis absorption spectrum of gold nanoparticles synthesized by *Balanites aegyptiaca* mesocarp aqueous extract.

A method for preparing nanoparticles using the aqueous extract of the *Balanites aegyptiaca* (L.) plant, referred to herein as "desert date" is provided. The nanoparticles can include metal, metal oxide nanoparticles, or *Balanites aegyptiaca* (L.) nanoparticles. The method can include: providing a metal salt solution comprising metal ions; providing desert date extract solution; and combining the metal ion solution and the desert date extract solution while stirring at a temperature in the range of 25° C. to 100° C. to produce the metal/metal oxide nanoparticles. The combining of the extract and the aqueous solution occurs at a temperature in the range of 50° C. to 100° C. and preferably at 90° C. The metal salt can include chloroauric acid ($HAuCl_4$) having a concentration of about 0.001 mol/L to about 0.005 mol/L, during the reduction when the nanoparticles to be synthesized are gold nanoparticles. Alternatively, the metal salt solution can include zinc nitrate hexahydrate $Zn(NO_3)_2 \cdot 6H_2O$ having a concentration of about 0.5 mol/L when the nanoparticles to be synthesized are zinc oxide nanoparticles. The formation of the gold or zinc oxide nanoparticles can be monitored using a spectrophotometer. Typically, the metal/metal oxide nanoparticles have a mean diameter in the range of from about 5 nm to about 200 urn and the nanoparticles are spherical, spheroidal, elongated spherical, rod-shaped and/or faceted. The extract of desert date can be prepared by soaking fruit powder of the desert date in water for about 12 hours and isolating the extract by centrifugation at about 5000 rpm.

A method of synthesizing *Balanites aegyptiaca* nanoparticles can include dissolving *Balanites aegyptiaca* powder in an organic solvent to form a solution; adding the solution to boiling water under ultrasonic conditions to form a mixture; and stirring the mixture at a temperature of about 24° C. and a speed of about 2000 rpm to obtain *Balanites aegyptiaca* nanoparticles.

The biosynthesized metal, metal oxide, and/or *Balanites aegyptiaca* nanoparticles can be used in inhibiting the growth or proliferation of a cancer cell. For example, the cancer cell can be contacted with an effective amount of the metal, metal oxide, and/or *Balanites aegyptiaca* nanoparticles, synthesized according to the present methods. The cancer cell can be lung cancer or colon cancer, but is not limited to these cancers.

The biosynthesized metal, metal oxide, and/or *Balanites aegyptiaca* nanoparticles can be used in inhibiting microbial activity. For example, an effective amount of the metal, metal oxide, and/or *Balanites aegyptiaca* nanoparticles can be administered to a site of microbial activity. The microorganisms can be selected from the group consisting of fungi, gram positive and gram negative bacteria.

As used herein, the term "Nanoparticle" refers to a particle having at least one dimension and sized between 1 and 100 nanometers. In some embodiments, the nanoparticles disclosed herein are from about 5 nm to about 500 nm in diameter. The term "effective amount," as used herein and in the claims, refers to an amount of the nanoparticles sufficient to prevent, ameliorate, treat and/or lessen the cancer or microbial activity.

The present teachings will be understood more readily by reference to the following examples, which are provided by way of illustration.

Example 1

Preparation of Crude Plant Materials

*Balanites aegyptiaca* (L.) Delile fruits were collected from Halayeb Triangle, Egypt, in July-August 2012. A voucher specimen (B.E.F.1) was deposited in the Herbarium of the Pharmacogonsy Department, Faculty of Pharmacy, Helwan University, Cairo, Egypt. The epicarps of the fruits were removed by hand. Exactly 20 g of fruits (excluding the mesocarp) were exhaustively extracted with distilled $H_2O$ by maceration overnight (3×50 ml). The extract was filtered and the combined filtrates were used for the preparation of the nanoparticles, which were afterwards immediately used for performing biological studies.

Example 2

Synthesis of Gold Nanoparticles (AuNPs)

Figure 2:
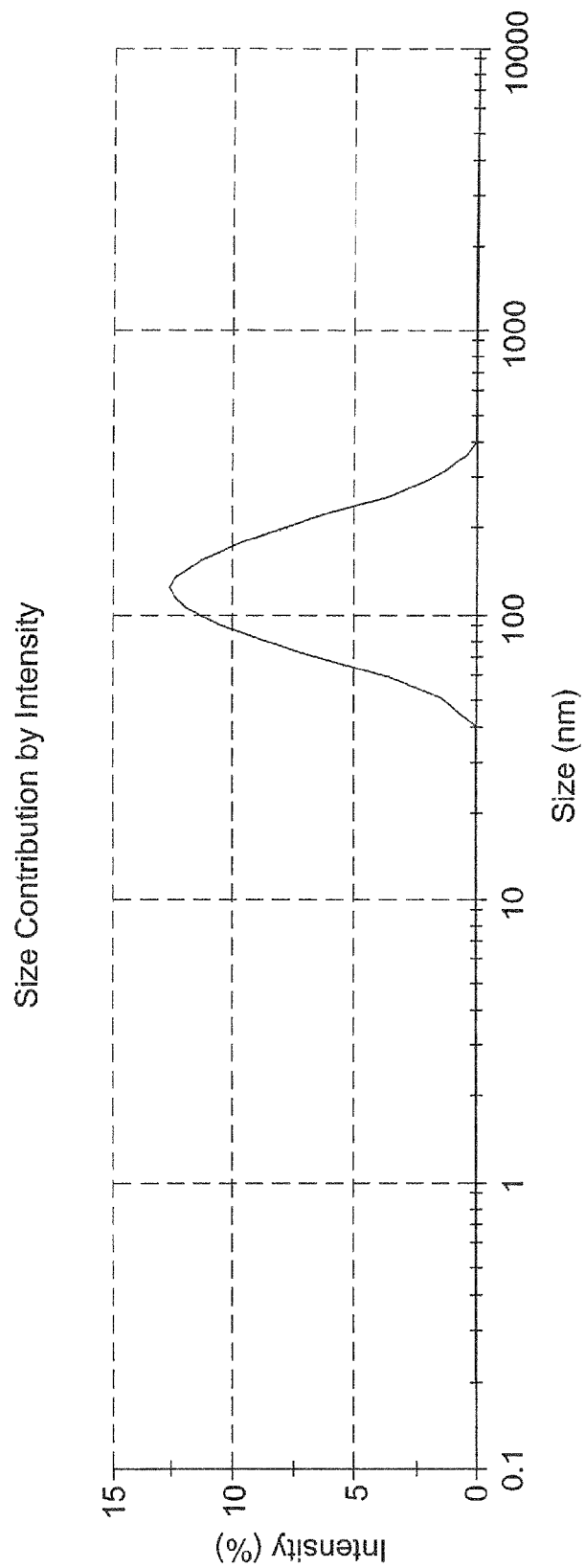
FIG. 2 shows a graph of the particles size distribution of *Balanites aegyptiaca* mesocarp gold nanoparticles.
Figure 3A:
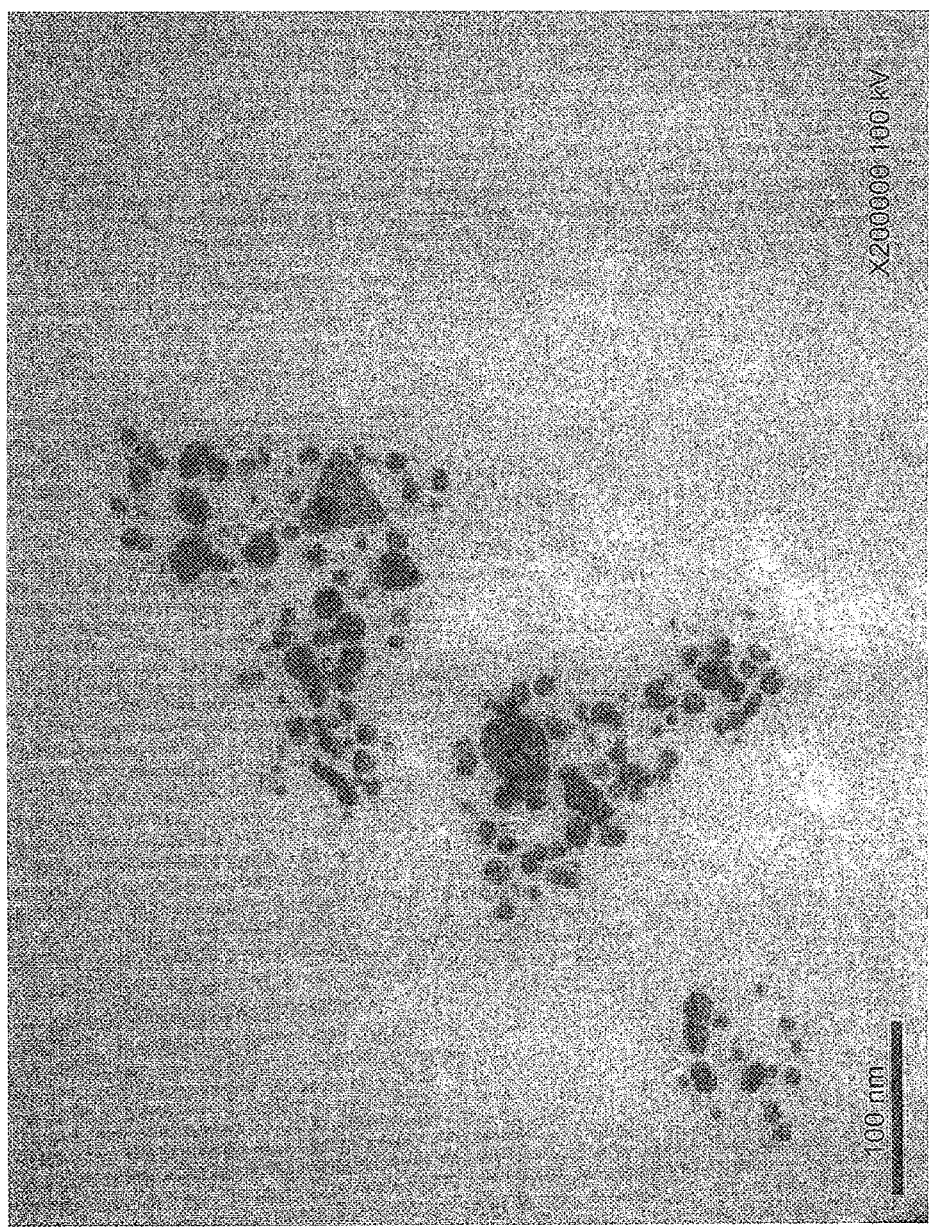
FIG. 3A shows the transmission electron microscopy (TEM) images of the gold nanoparticles produced by the present method.
Figure 3B:
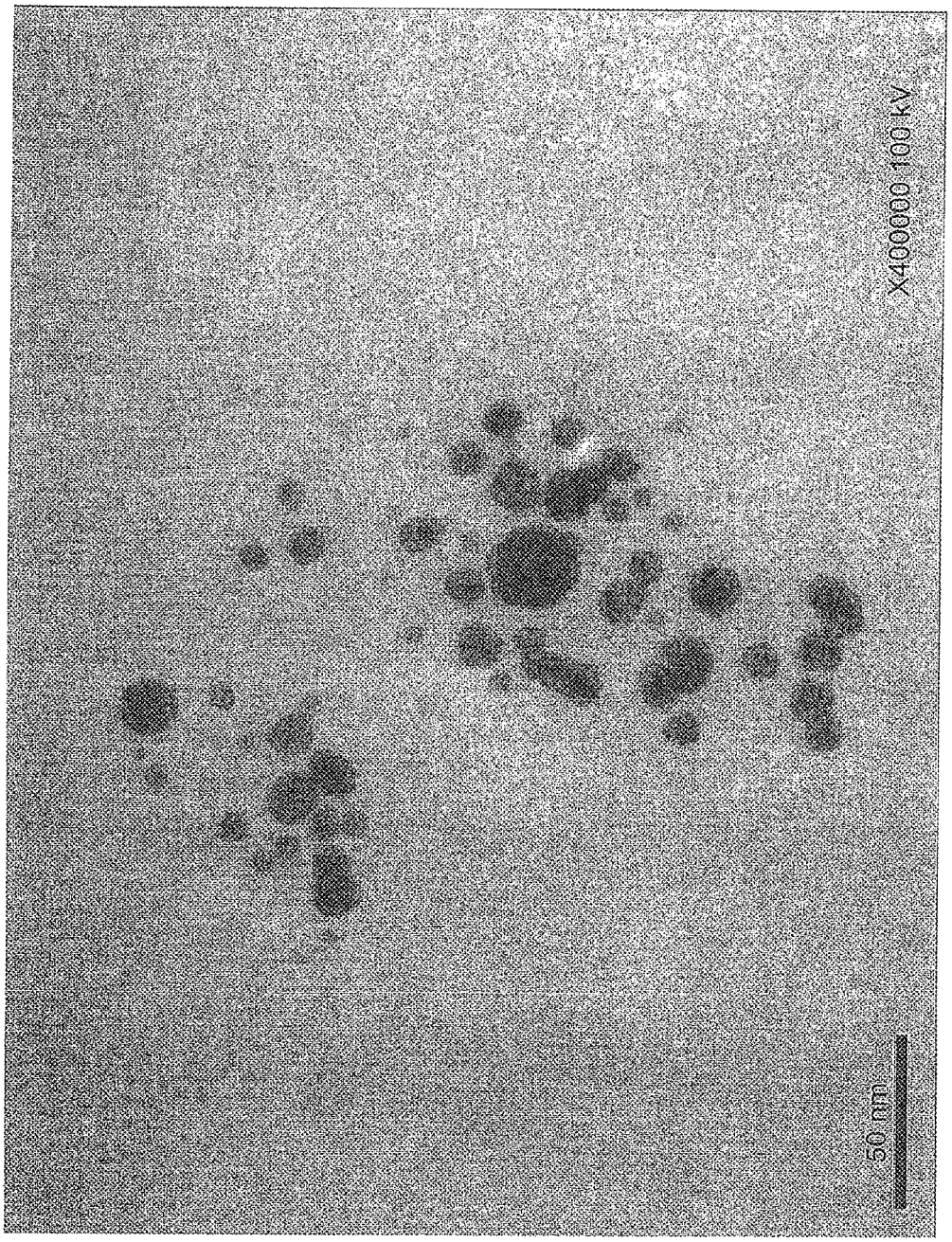
FIG. 3B shows the transmission electron microscopy (TEM) images of the gold nanoparticles produced by the present method.
Figure 3C:
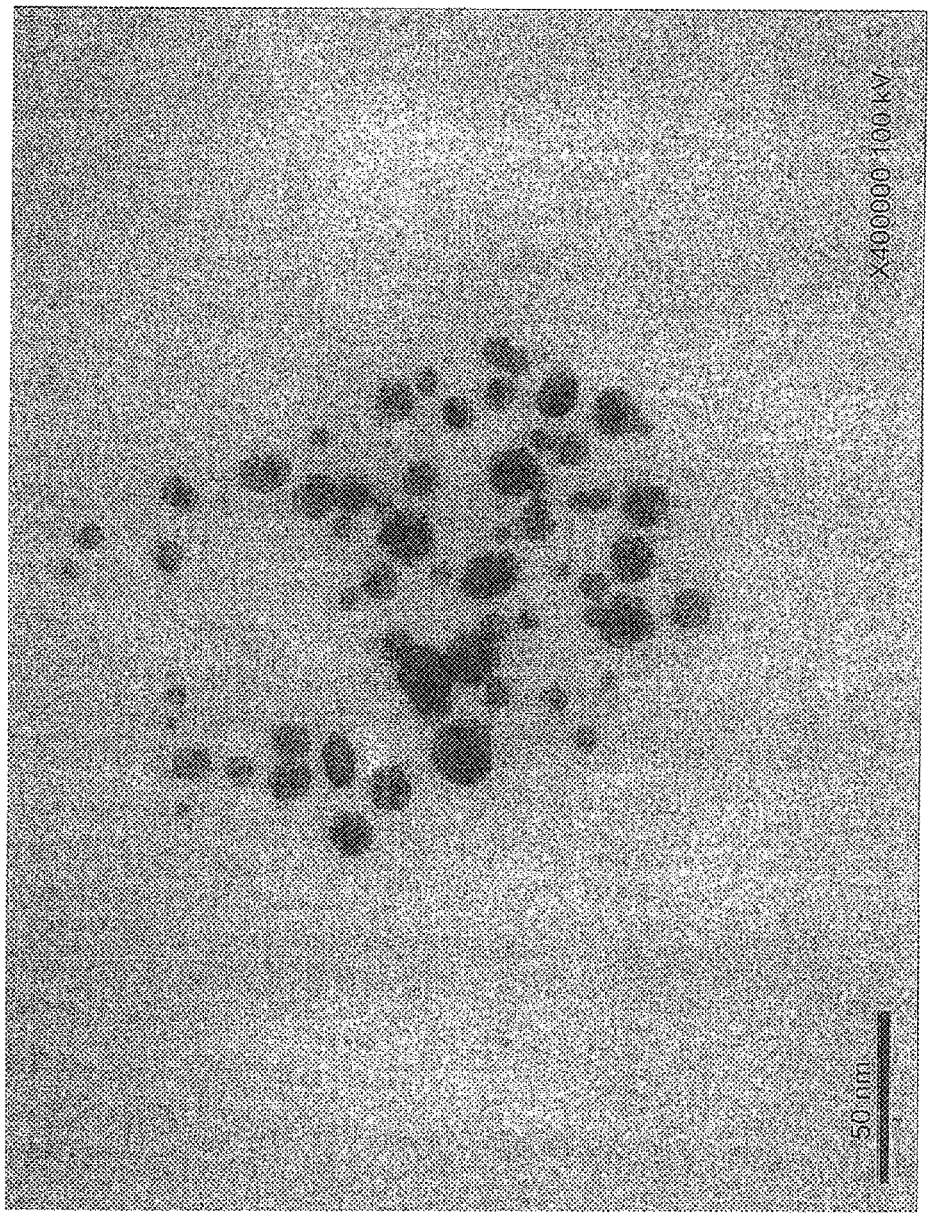
FIG. 3C shows the transmission electron microscopy (TEM) images of the gold nanoparticles produced by the present method.
Figure 3D:
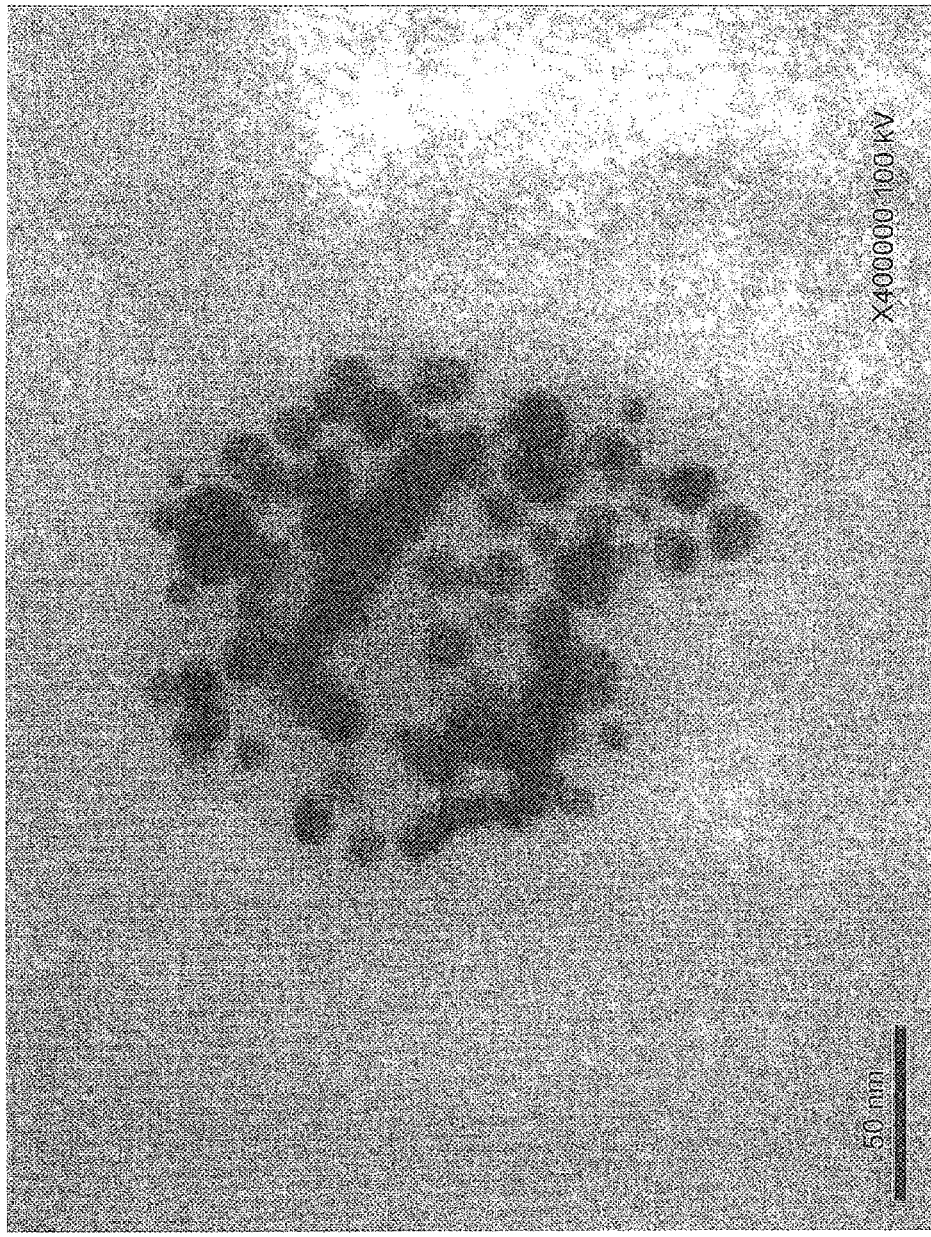
FIG. 3D shows the transmission electron microscopy (TEM) images of the gold nanoparticles produced by the present method.

For green synthesis of gold nanoparticles, the reagent Chloroauric acid (analytical grade, $HAuCl_4$) received from LobaChemie, India, was used without further purification. *B. aegyptiaca* aqueous extract was centrifuged for 15 minutes at 5000 rpm at room temperature. This was followed by dropwise addition of 5 ml of the plant extract to the light yellow colored aqueous solution of 0.001 mol/L Chloroauric acid at 70° C., while stirring magnetically at 1000 rpm for 10 min. The change in color observed during this treatment indicated the reduction of gold ions into gold particles and the formation of gold nanoparticles (AuNPs). The formation of AuNPs was verified by the development of its characteristic red color, due to excitation of surface plasmon resonance band in the UV-visible region as illustrated in FIG. 1. FIG. 2 shows a graph of the particle size distribution of *Balanites aegyptiaca* mesocarp gold nanoparticles.

Transmission electron microscopy (TEM, JEM-1011, JEOL, Japan) was employed to characterize the size, shape and morphologies of formed biogenic synthesized gold nanoparticles. A drop of gold nanoparticles suspension was deposited on carbon coated copper grid and the film on grid was then dried. The TEM was operated and the measurements were performed at accelerating voltage of 100 KV. FIGS. 3A-3D shows the transmission electron microscopy (TEM) images of the gold nanoparticles produced by the present method.

Figure 4A:
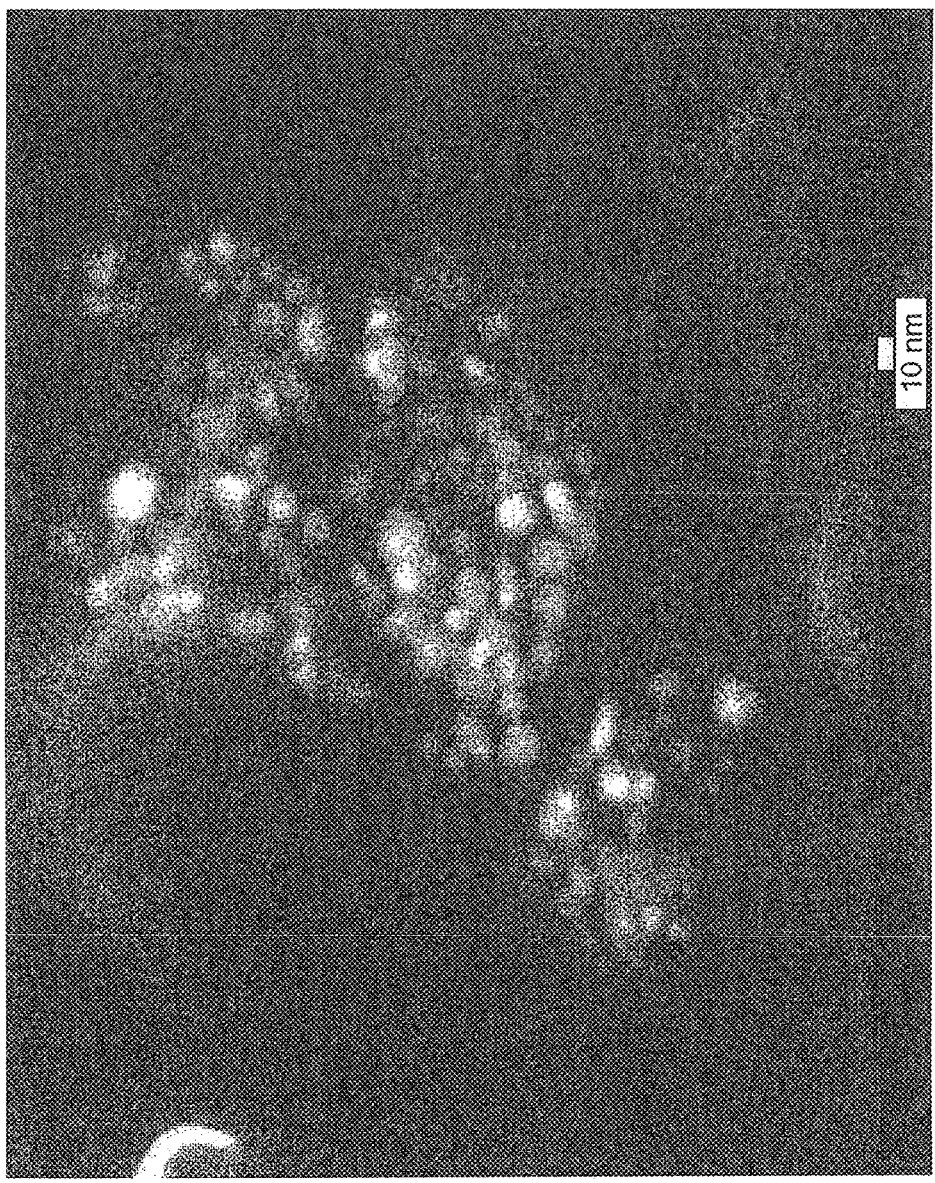
FIGS. 4A and 4B shows the SEM micrographs of *Balanites aegyptiaca* mesocarp gold nanoparticles.
Figure 4B:

Scanning electron microscopy (SEM) was employed to characterize the shape and morphologies of formed biogenic synthesized gold nanoparticles using JEOL-FESEM; and Energy Dispersive Spectrometer (EDS) analysis was performed for the confirmation of elemental gold. The samples were dried at room temperature and then analyzed for samples composition of the synthesized nanoparticles. Elemental analysis on single particles was carried out using Oxford Instrument, Incax-act, equipped with Scanning electron microscopy. Table 1 shows the EDS results displaying the percentage of elements present in *Balanites aegyptiaca* gold nanoparticle suspension. FIGS. 4A and 4B shows the SEM micrographs of *Balanites aegyptiaca* mesocarp gold nanoparticles.

Figure 5A:
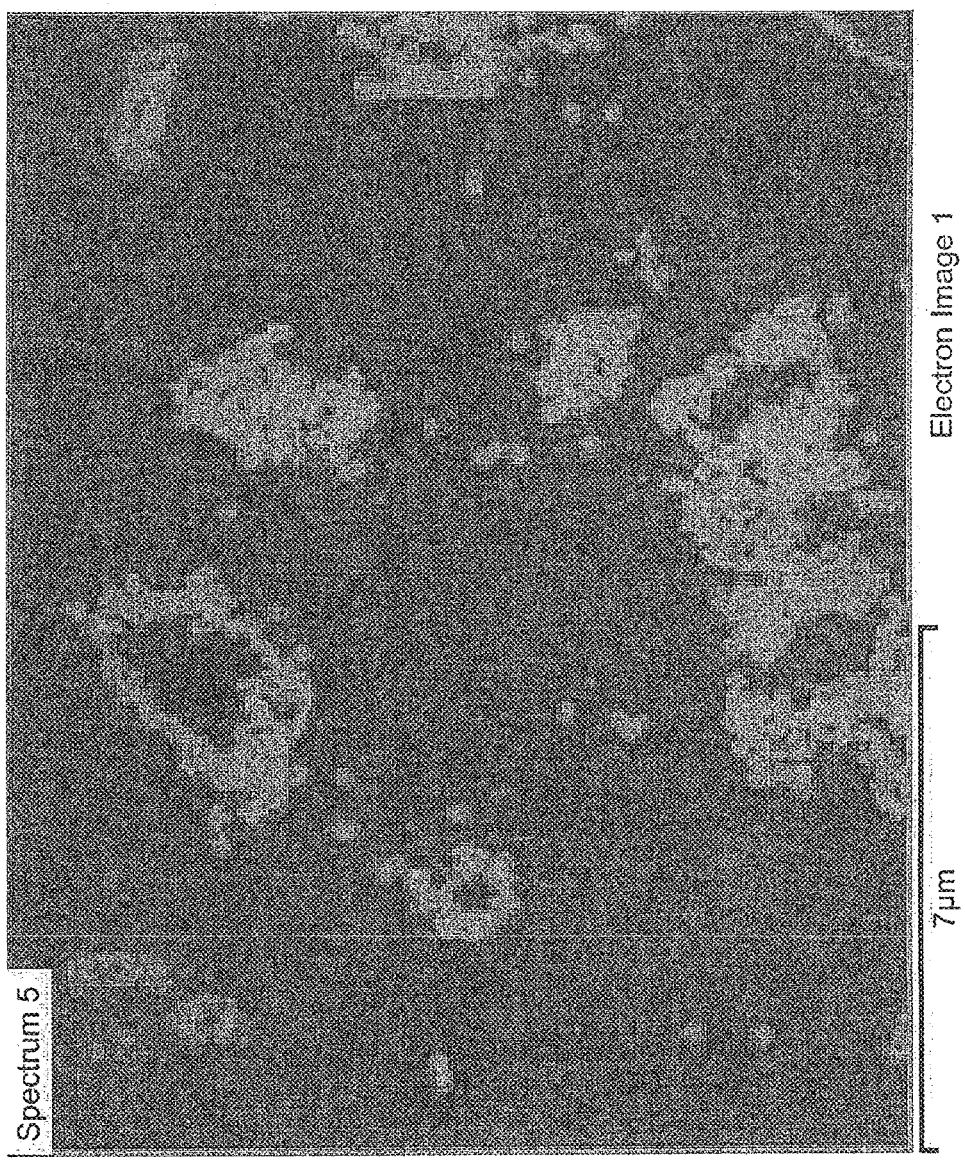
FIG. 5A shows an SEM micrograph of *Balanites aegyptiaca* mesocarp nanoparticles.
Figure 5B:
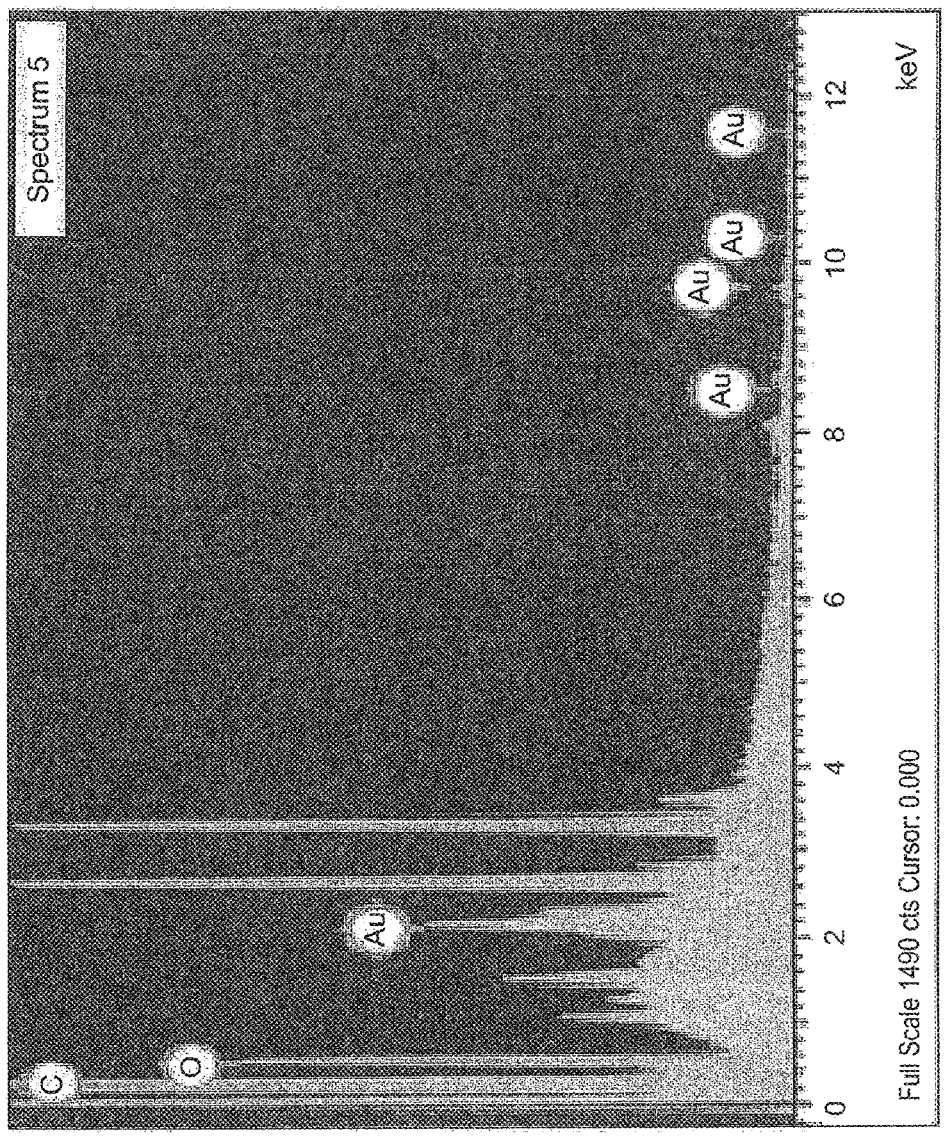
FIG. 5B is a graph of the Energy Dispersive Spectrum (EDS) pattern of *Balanites aegyptiaca* nanoparticles with four dominant peaks for carbon, oxygen and gold atoms, respectively.

FIG. 5A shows an SEM micrograph of *Balanites aegyptiaca* mesocarp nanoparticles. FIG. 5B is a graph of the Energy Dispersive Spectrum (EDS) pattern of the *Balanites aegyptiaca* nanoparticles with four dominant peaks for carbon, oxygen and gold atoms, respectively. Table 1 shows the EDS results showing percentage of elements present in *Balanites aegyptiaca* gold nanoparticle suspension.

TABLE 1

| Element | Weight | Atomic % |
|---------|--------|----------|
| C K     | 82.67  | 87.98    |
| O K     | 14.85  | 11.86    |
| Au M    | 2.48   | 0.16     |
| Totals  | 100.00 |          |

Figure 6A:
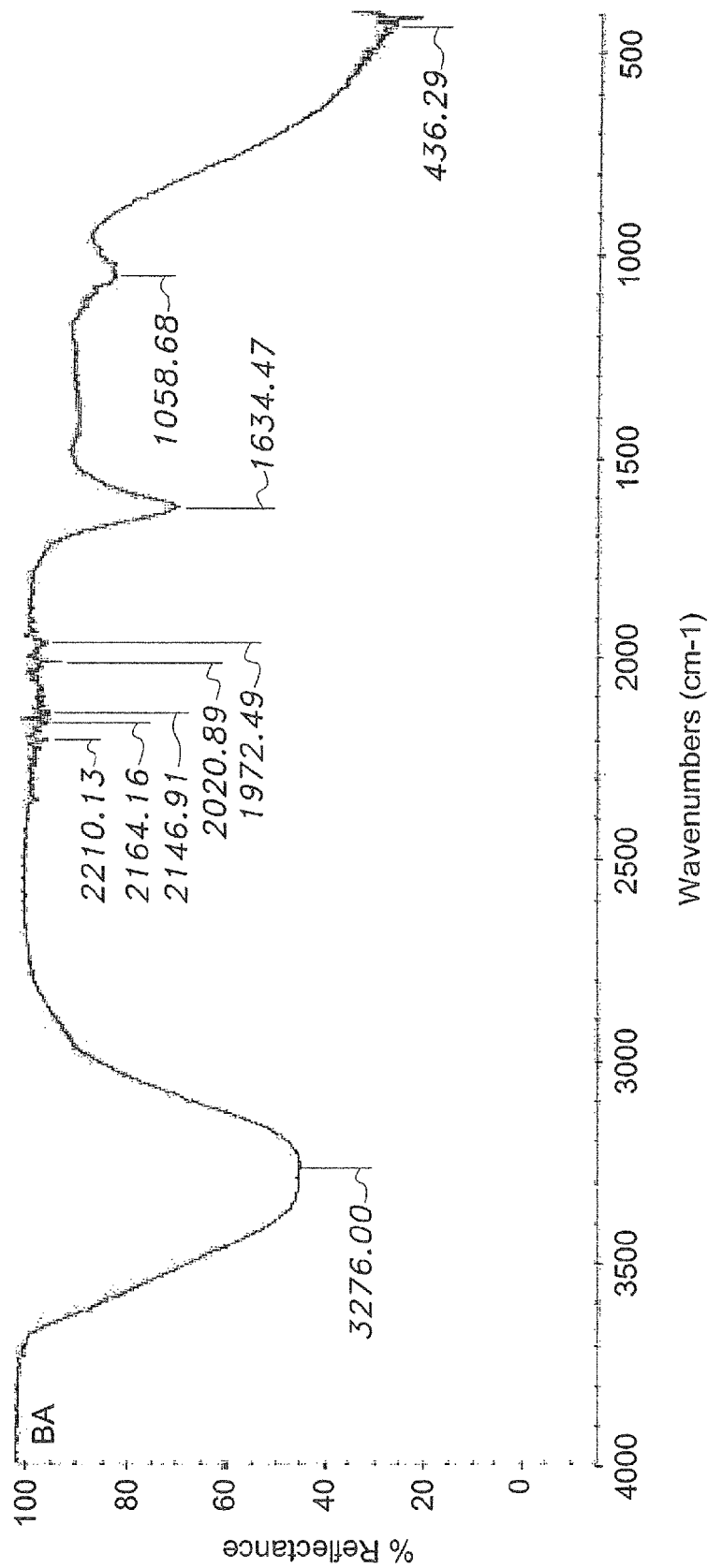
FIG. 6A shows the Fourier Transform Infrared Spectroscopy (FTIR) spectra of *Balanites aegyptiaca* extract and FIG. 6B shows the *Balanites aegyptiaca* synthesized gold nanoparticles.
Figure 6B:
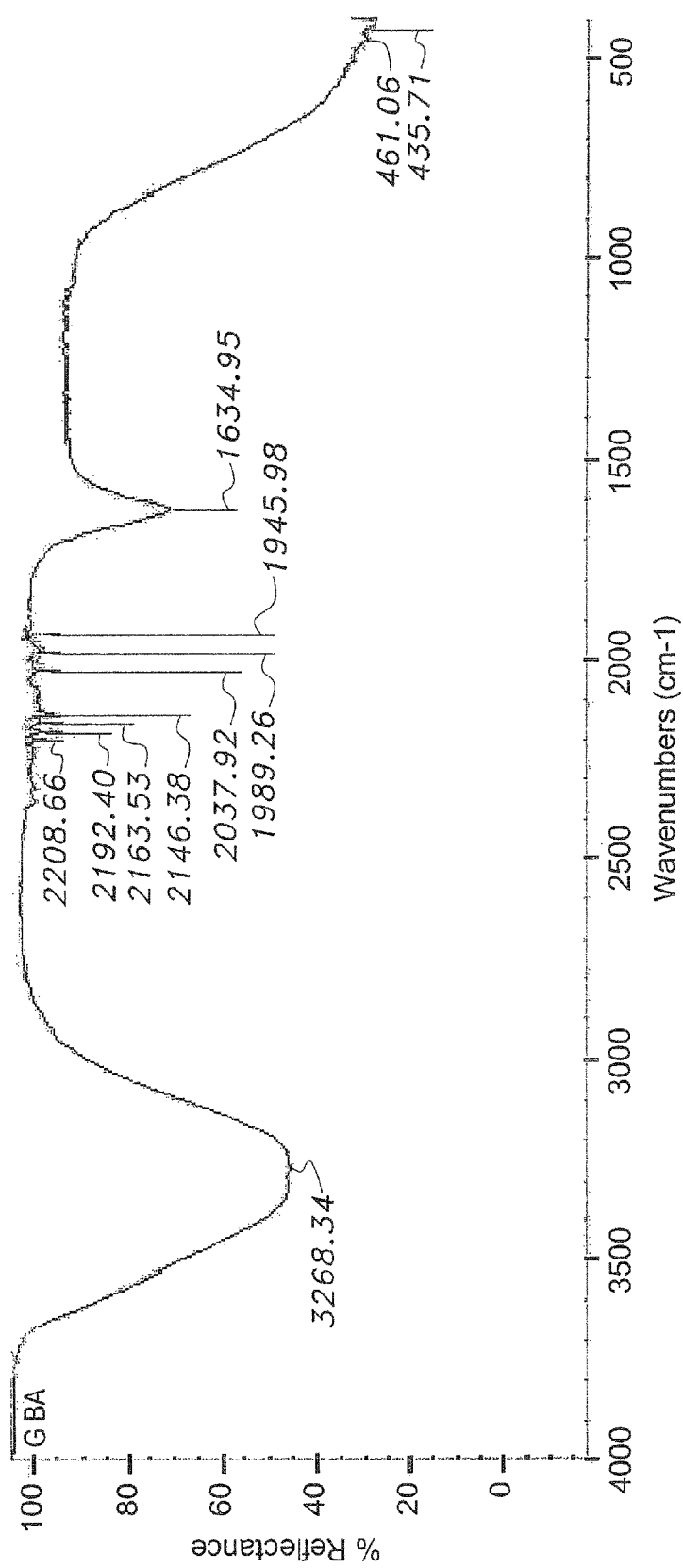

FIG. 6A illustrated the Fourier Transform Infrared Spectroscopy (FTIR) spectra of *Balanites aegyptiaca* extract and FIG. 6B shows the *Balanites aegyptiaca* synthesized gold nanoparticles.

Example 3

Synthesis of Zinc Oxide Nanoparticles (ZnO)

Figure 7A:
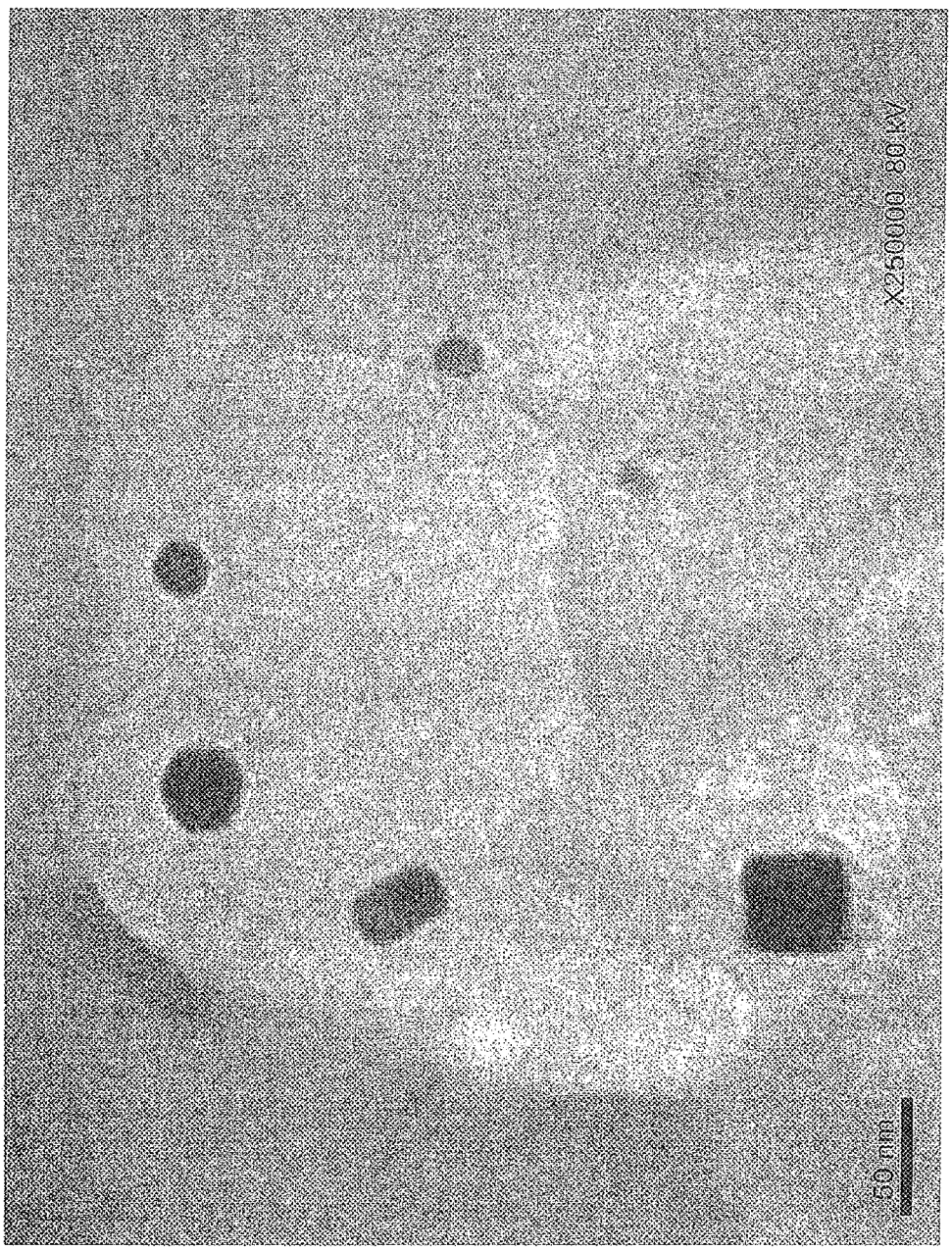
FIGS. 7A and 7B show the graph of Transmission Electron Microcopy (TEM) image of *Balanites aegyptiaca* zinc nanoparticles.
Figure 7B:
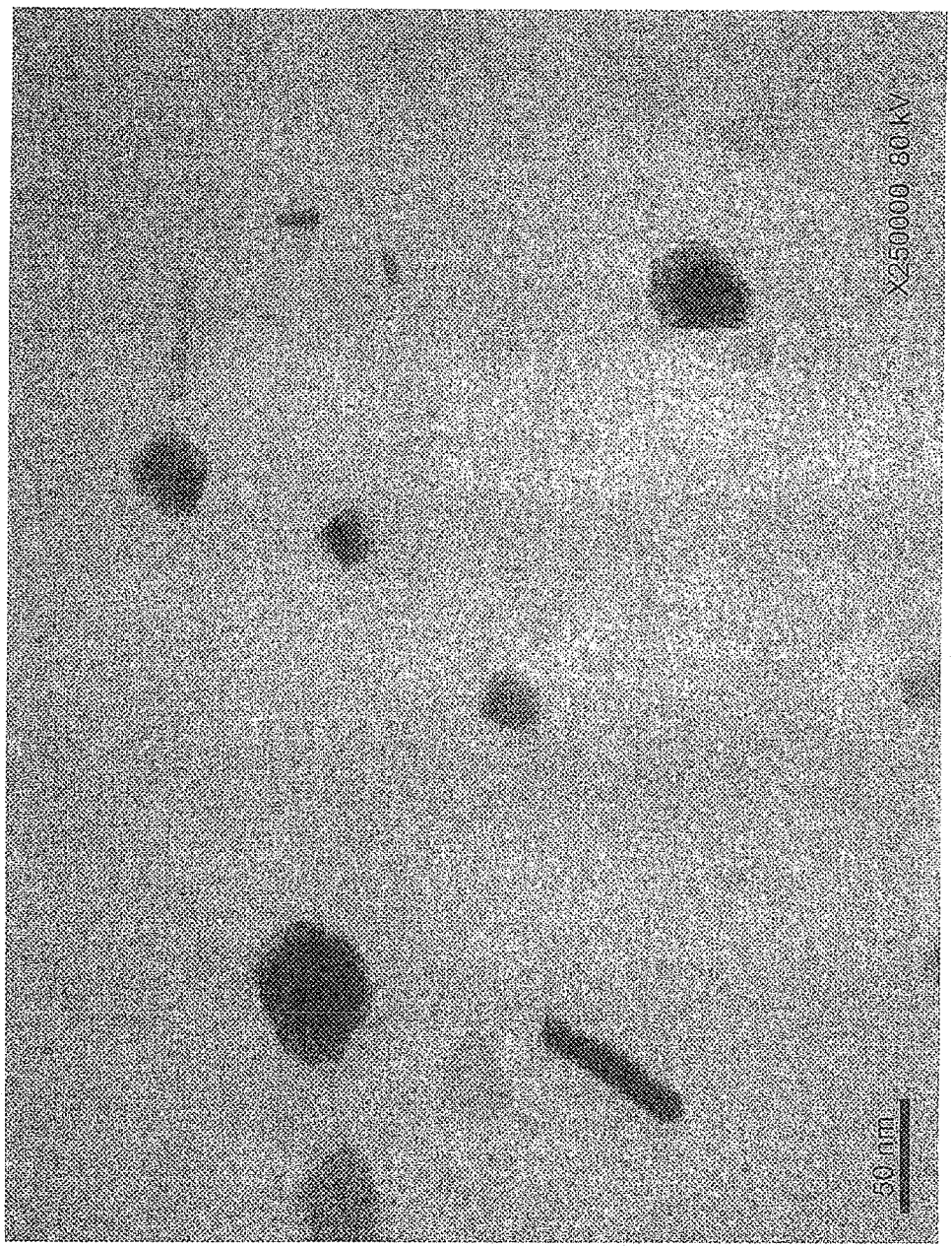

A first method of synthesis of zinc oxide nanoparticles using *Balanites aegyptiaca* extract included dissolving 0.5 M zinc nitrate hexahydrate, $Zn(NO_3)_2.6H_2O$ in 50 ml *Balanites aegyptiaca* extract and stirring at 90° C. until it was reduced to a brown colored paste. The paste was then dried to get a brown powder including ZnO nanoparticles. A second method of synthesis of zinc oxide nanoparticles using *Balanites aegyptiaca* extract included adding drops of 1 M of sodium hydroxide (NaOH) to a boiling solution of 0.5 M zinc nitrate hexahydrate $Zn(NO_3)_2.6H_2O$ and *Balanites Aegyptiaca* extract under stirring. After a brown paste appeared, the paste was dried in the oven, and a dried powder was then collected. The powder included zinc oxide nanoparticles. A third method of synthesis of zinc oxide nanoparticles using *Balanites aegyptiaca* extract included dissolving in a three-neck glass flask 1 M of NaOH in *Balanites Aegyptiaca* extract; heating the resulting solution under constant stirring to a temperature of 90° C., then slowly adding (dripping for 60 minutes) a solution of 0.5 M zinc nitrate hexahydrate $Zn(NO_3)_2.6H_2O$ into the three-neck glass flask containing the NaOH aqueous solution and *Balanites Aegyptiaca* extract under continual stirring. In this procedure the reaction temperature was constantly maintained at 90° C. The paste was dried at 65° C. in an oven for several hours. FIGS. 7A and 7B presents a graph of Transmission electron microscopy (TEM) image of *Balanites aegyptiaca* zinc oxide nanoparticles. FIGS. 7A and 7B show the graph of Transmission Electron Microcopy (TEM) image of *Balanites Aegyptiaca* zinc nanoparticles.

Example 4

Synthesis of *Balanites aegyptiaca* Nanoparticles (without Metals)

Figure 8A:
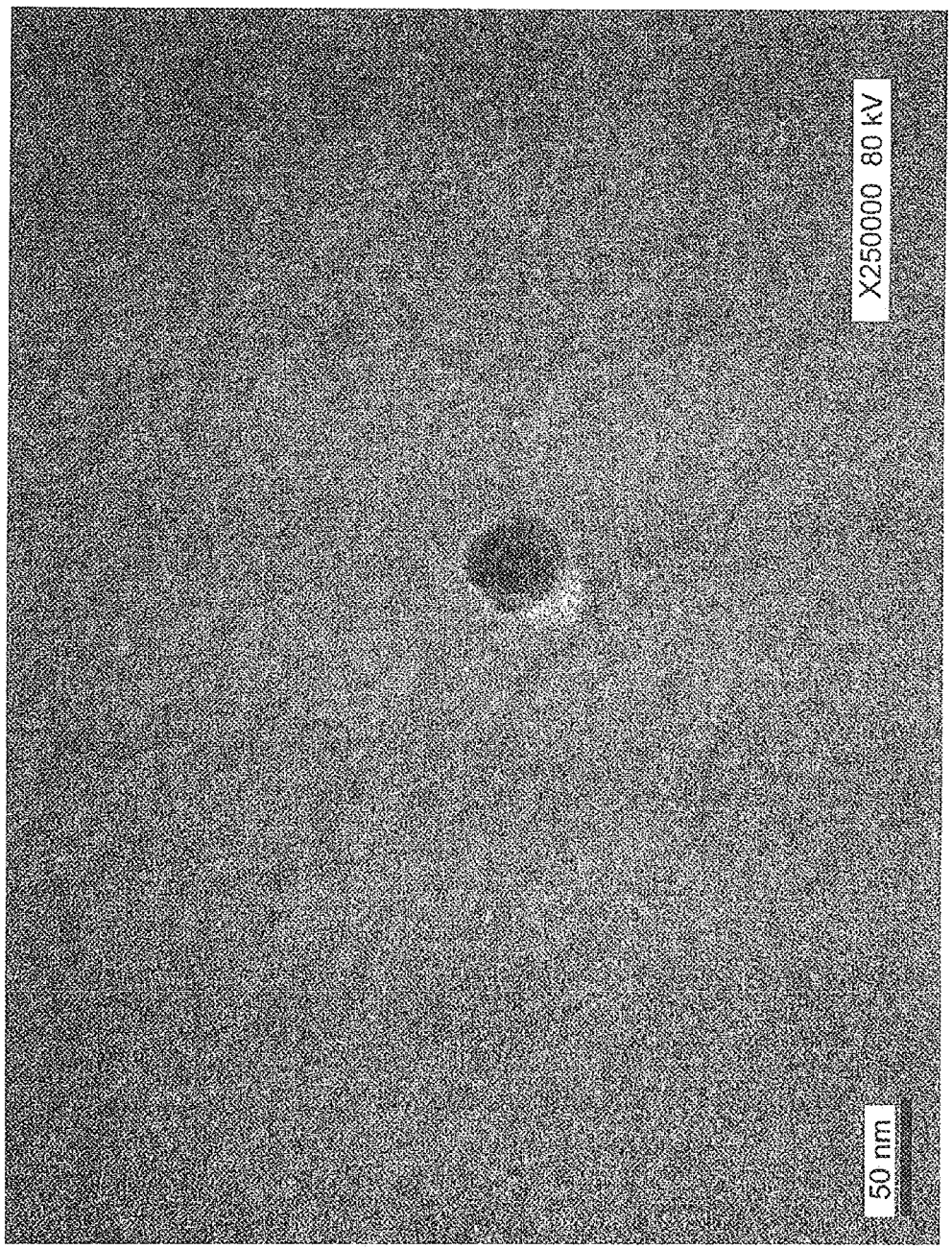
FIGS. 8A and 8B show the graph of TEM of *Balanites aegyptiaca* without the metals.
Figure 8B:
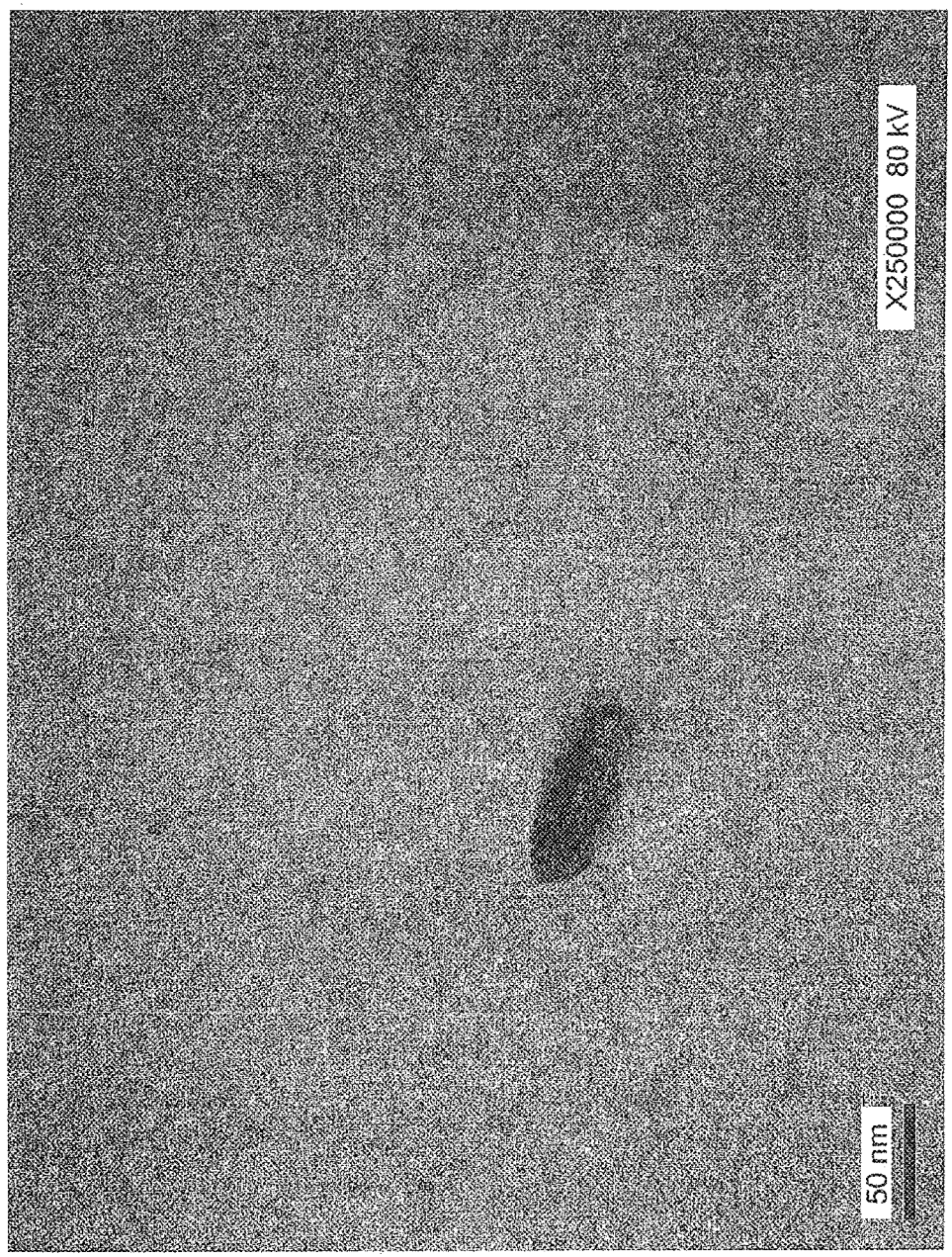

For synthesis of *Balanites aegyptiaca* nanoparticles, 50 mg of *Balanites aegyptiaca* powder was dissolved in 50 ml of methanol. Then, 1 mL of this solution was sprayed into boiling water (70 mL) dropwise under ultrasonic conditions. After sonication for 15 min, the contents were stirred at 2000 rpm at room temperature for about 20 min to obtain *Balanites Aegyptiaca* nanoparticles. FIGS. 7A and 7B represent a graph of Transmission Electron Microscopy (TEM) image of *Balanites aegyptiaca* nanoparticles (without metals). FIGS. 8A and 8B show the graph of TEM of *Balanites aegyptiaca* without metals.

Figure 13:
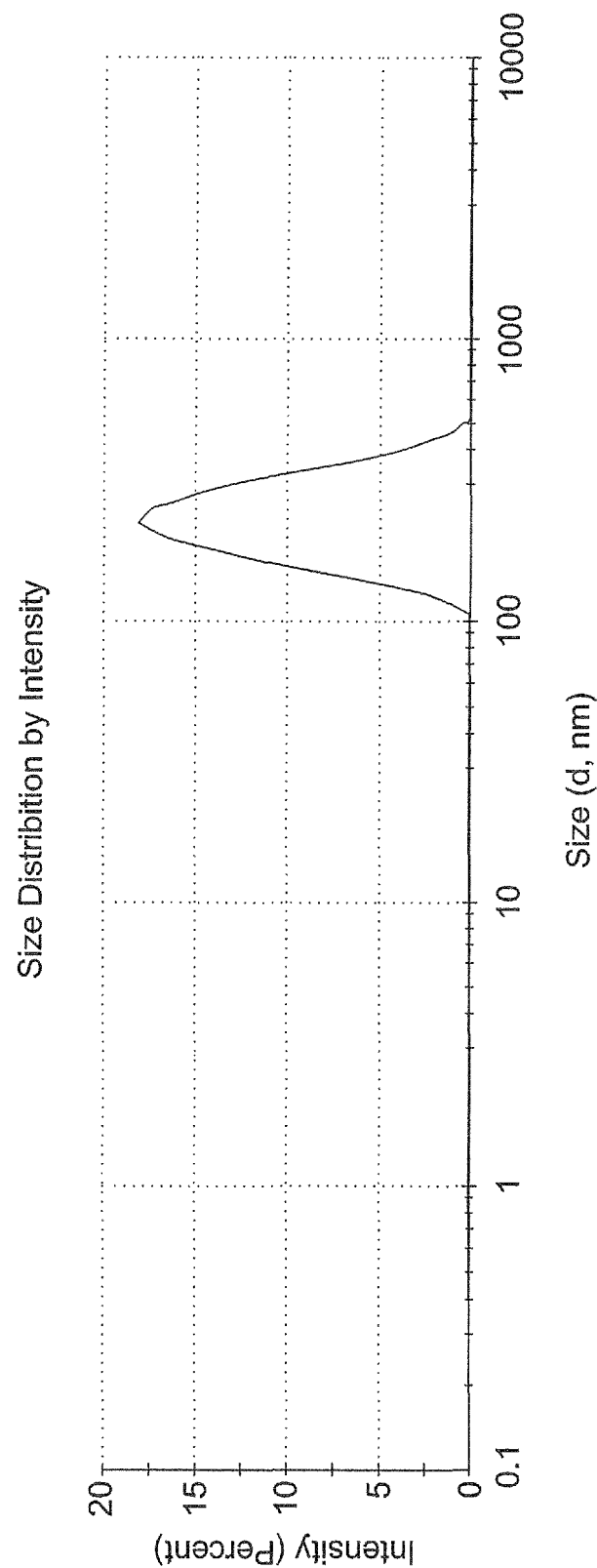
FIG. 13 shows a graph of the particles size distribution of *Balanites aegyptiaca* mesocarp nanoparticles (without metal).

The synthesized gold, zinc oxide and *Balanites Aegyptiaca* nanoparticles were characterized using UV-visible spectroscopy analyses using a Perkin Elmer UV-visible spectrometer (Lambda 25, PerkinElmer, United Kingdom). Thermo scientific, Nicolet 6700, FT-IR spectrophotometer was used for recording the infrared (IR) spectrum, while the Zetasizer, Nano series, HT Laser, ZEN3600 from Molvern Instrument, UK was used for the size determination of nanoparticles. FIG. 13 shows a graph of the particles size distribution of *Balanites aegyptiaca* mesocarp nanoparticles (without metal).

Example 5

Antitumor Activity Assay

The tested human carcinoma cell lines were obtained from the American Type Culture Collection (ATCC, Rockville, Md.). The cells were grown on RPMI-1640 medium supplemented with 10% inactivated fetal calf serum and 50 µg/ml gentamycin. The cells were maintained at 37° C. in a humidified atmosphere with 5% $CO_2$ and were sub cultured two to three times a week.

For antitumor assays, the tumor cell lines were suspended in medium at concentration $5 \times 10^4$ cell/well in Corning® 96-well tissue culture plates, then incubated for 24 hours. The tested compounds were then added into 96-well plates (six replicates) to achieve eight concentrations for each compound. Six vehicle controls with media or 0.5% DMSO were run for each 96 well plate as a control. After incubating for 24 h, the numbers of viable cells were determined by the MTT test. Briefly, the media was removed from the 96 well plate and replaced with 100 µl of fresh culture RPMI 1640 medium without phenol red then 10 µl of the 12 mM MTT stock solution (5 mg of MTT in 1 mL of PBS) to each well including the untreated controls. The 96 well plates were then incubated at 37° C. and 5% $CO_2$ for 4 hours. An 85 µl aliquot of the media was removed from the wells, and 50 µl of DMSO was added to each well and mixed thoroughly with the pipette and incubated at 37° C. for 10 min. Then, the optical density was measured at 590 nm with the microplate reader (SunRise, TECAN, Inc., USA) to determine the number of viable cells and the percentage of viability was calculated using the equation below where ODt is the mean optical density of wells treated with the tested sample and ODc is the mean optical density of untreated cells:

$$\% \text{ of Cell Viability} = \left[1 - \frac{(ODt)}{(ODc)}\right] \times 100 \quad (1)$$

The relation between surviving cells and drug concentration is plotted to get the survival curve of each tumor cell line after treatment with the specified compound. The 50% inhibitory concentration ($IC_{50}$), the concentration required to cause toxic effects in 50% of intact cells, was estimated from graphic plots of the dose response curve for each conc. using Graphpad Prism software (San Diego, Calif. USA).

The potential cytotoxic effect of the synthesized nanoparticles was evaluated against two cell lines, namely the human lung adenocarcinoma epithelial cell line A549 (Table 3) and the human colon carcinoma cells HCT-116 (Table 2). Results showed percentage inhibition above 80% for the synthesized gold nanoparticles, as displayed in Tables 2 and 3 respectively.

TABLE 2

| Sample conc. (µl) | Viability % (3 Replicates) | | | | Inhibition % | Standard Deviation (±) |
|---|---|---|---|---|---|---|
| | 1st | 2nd | 3rd | Mean | | |
| 100 | 15.29 | 17.21 | 19.86 | 17.45 | 82.55 | 2.29 |
| 50 | 29.04 | 27.78 | 34.71 | 30.51 | 69.49 | 3.69 |
| 25 | 48.37 | 44.51 | 46.28 | 46.39 | 53.61 | 1.93 |
| 12.5 | 70.38 | 69.24 | 63.69 | 67.77 | 32.23 | 3.58 |
| 6.25 | 72.54 | 80.42 | 77.54 | 76.83 | 23.17 | 3.99 |
| 3.125 | 85.92 | 89.36 | 90.14 | 88.47 | 11.53 | 2.25 |
| 0 | 100 | 100 | 100 | 100 | 0.00 | |

Table 3 shows the evaluation of cytotoxicity of the synthesized gold nanoparticles against A549 cell line.

TABLE 3

| Sample conc. (µl) | Viability % (3 Replicates) | | | | Inhibition % | Standard Deviation (±) |
|---|---|---|---|---|---|---|
| | 1st | $2^{nd}$ | 3rd | Mean | | |
| 100 | 12.88 | 10.97 | 13.92 | 12.59 | 87.41 | 1.50 |
| 50 | 27.92 | 26.28 | 30.41 | 28.20 | 71.80 | 2.08 |
| 25 | 39.45 | 37.88 | 42.57 | 39.97 | 60.03 | 2.39 |

TABLE 3-continued

| Sample | Viability % (3 Replicates) | | | | Inhibition | Standard Deviation |
|---|---|---|---|---|---|---|
| conc. (µl) | 1st | $2^{nd}$ | 3rd | Mean | % | (±) |
| 12.5 | 58.98 | 63.27 | 60.78 | 61.01 | 38.99 | 2.15 |
| 6.25 | 72.54 | 80.75 | 78.94 | 77.41 | 22.59 | 4.31 |
| 3.125 | 87.51 | 92.34 | 89.15 | 89.67 | 10.33 | 2.46 |
| 0 | 100 | 100 | 100 | 100 | 0.00 | |

Figure 9:
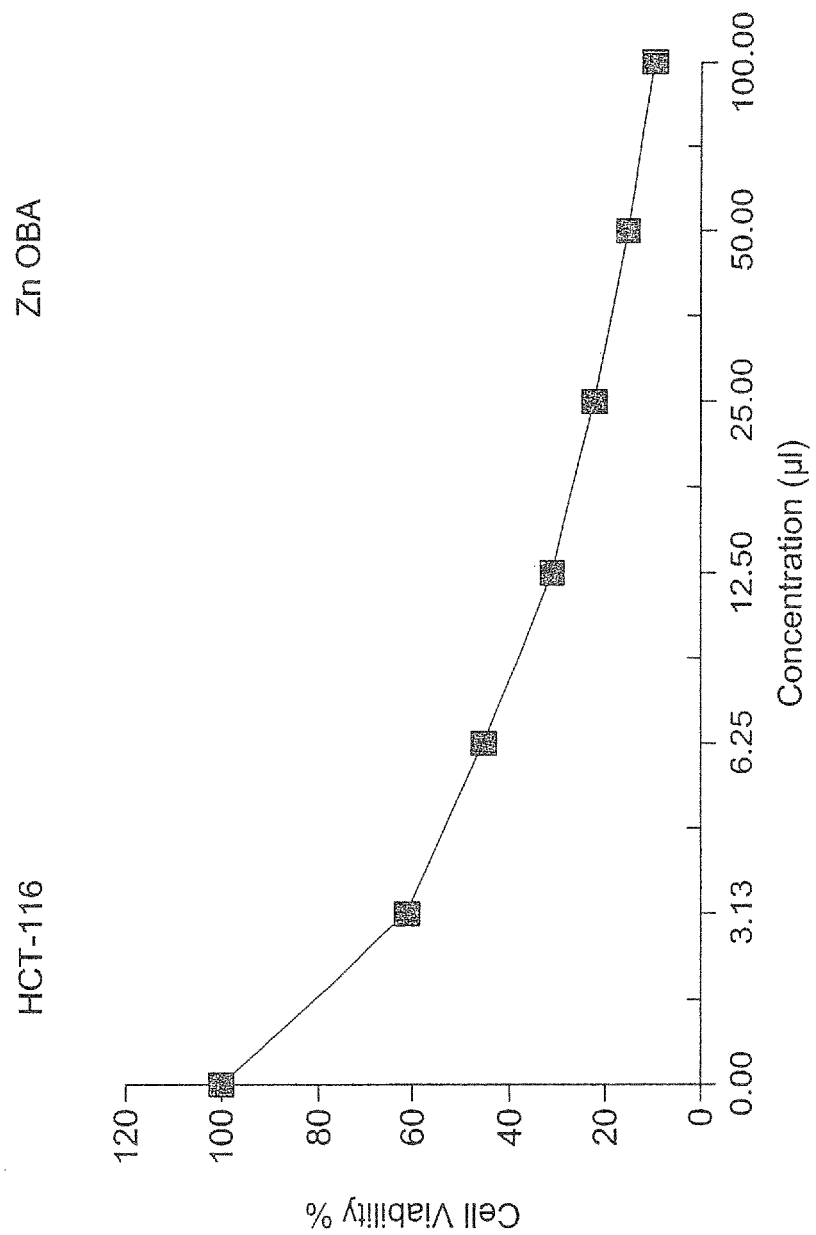
FIG. 9 shows the inhibitory activity of zinc oxide nanoparticles synthesized from *Balanites aegyptiaca* extract against colon carcinoma cells was detected under these experimental conditions with $IC_{50}$=5.31 µl.

FIG. 9 illustrates the inhibitory activity of zinc oxide nanoparticles against colon carcinoma cells using zinc oxide nanoparticles with an $IC_{50}$=5.31 µl. Table 4 shows the inhibitory activity results of zinc oxide nanoparticles synthesized by *Balanites aegyptiaca* against colon carcinoma cells.

TABLE 4

| Sample | Viability % (3 Replicates) | | | | Inhibition | Standard Deviation |
|---|---|---|---|---|---|---|
| conc. (µl) | $1^{st}$ | $2^{nd}$ | 3rd | Mean | % | (±) |
| 100 | 9.87 | 8.13 | 10.42 | 9.47 | 90.53 | 1.20 |
| 50 | 16.84 | 13.95 | 14.67 | 15.15 | 84.85 | 1.50 |
| 25 | 21.39 | 20.48 | 24.56 | 22.14 | 77.86 | 2.14 |
| 12.5 | 28.96 | 32.14 | 31.79 | 30.96 | 69.04 | 1.74 |
| 6.25 | 43.85 | 45.79 | 46.24 | 45.29 | 54.71 | 1.27 |
| 3.125 | 59.23 | 60.81 | 63.06 | 61.03 | 38.97 | 1.92 |
| 0 | 100 | 100 | 100 | 100 | 0.00 | |

Figure 10:
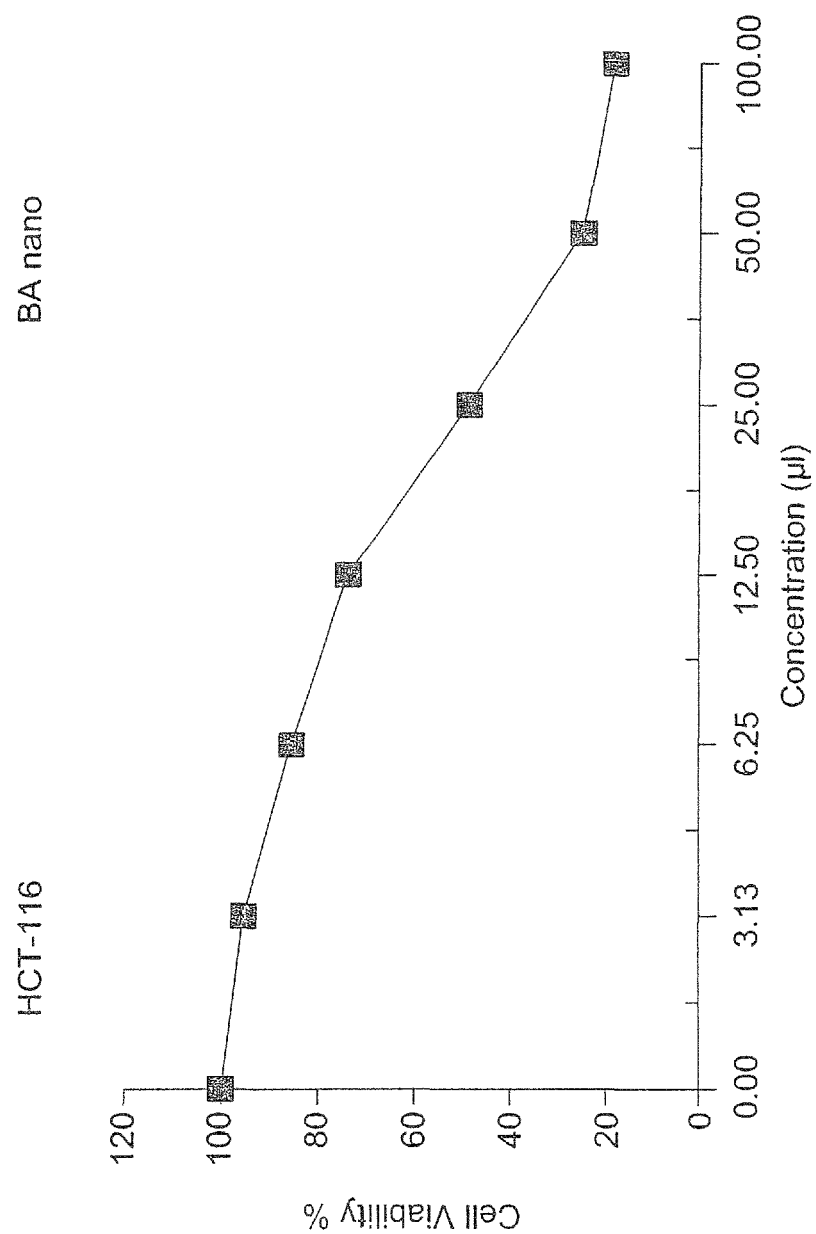
FIG. 10 shows the inhibitory activity of *Balanites aegyptiaca* nanoparticles against colon carcinoma cells.

FIG. 10 illustrates the inhibitory activity of *Balanites aegyptiaca* nanoparticles against colon carcinoma cells with an $IC_{50}$=24.3 µl. Table 5 shows the inhibitory activity results of *Balanites aegyptiaca* nanoparticles against colon carcinoma cells (the cell viability and the inhibition percentage as a function of the sample concentration).

TABLE 5

| Sample | Viability % (3 Replicates) | | | | Inhibition | Standard Deviation |
|---|---|---|---|---|---|---|
| conc. (µl) | $1^{st}$ | 2nd | 3rd | Mean | % | (±) |
| 100 | 16.92 | 17.14 | 20.86 | 18.31 | 81.69 | 2.21 |
| 50 | 24.21 | 26.08 | 23.95 | 24.75 | 75.25 | 1.16 |
| 25 | 48.37 | 50.94 | 46.23 | 48.51 | 51.49 | 2.36 |
| 12.5 | 79.28 | 68.72 | 72.41 | 73.47 | 26.53 | 5.36 |
| 6.25 | 88.41 | 86.25 | 81.54 | 85.40 | 14.60 | 3.51 |
| 3.125 | 96.78 | 95.84 | 93.22 | 95.28 | 4.72 | 1.84 |
| 0 | 100 | 100 | 100 | 100 | 0.00 | |

Figure 11:
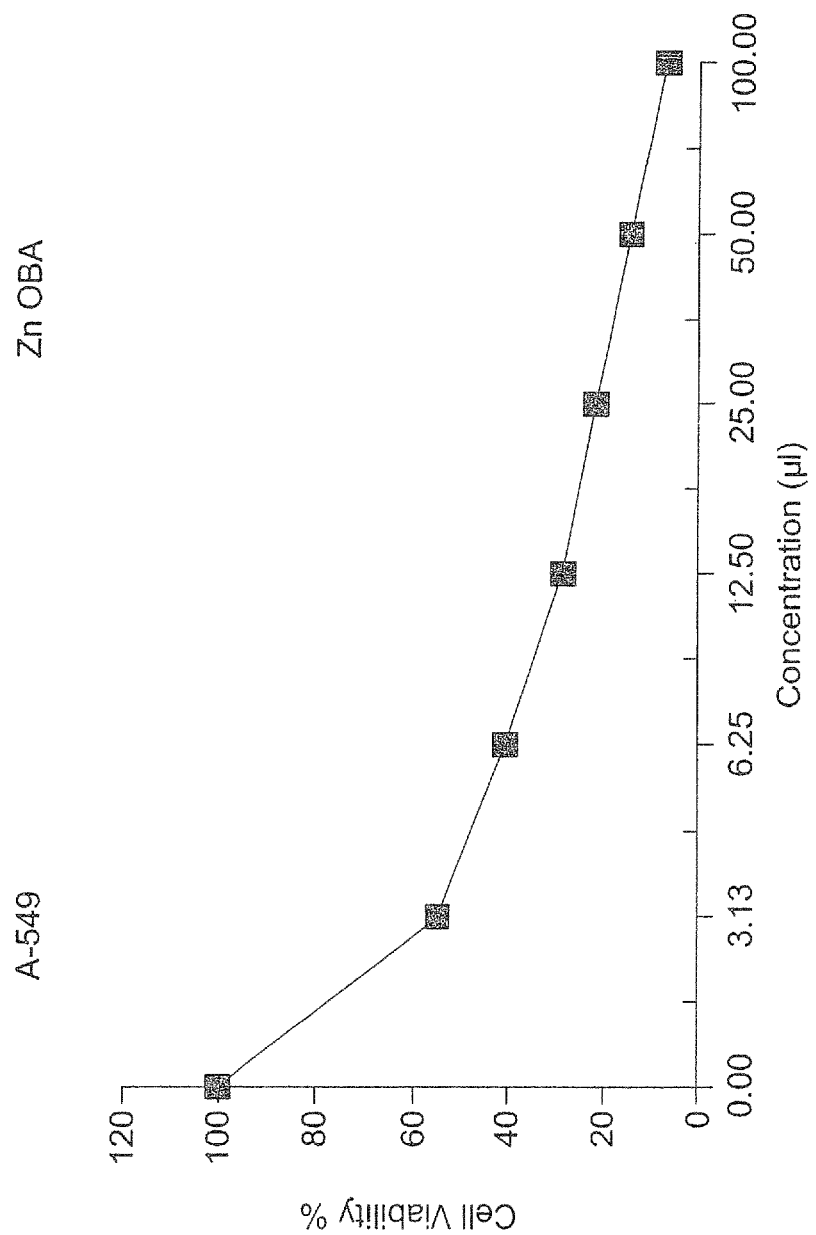
FIG. 11 is a graph showing the inhibitory activity of zinc oxide nanoparticles synthesized from *Balanites aegyptiaca* extract against lung carcinoma cells.

FIG. 11 shows the inhibitory activity of zinc oxide nanoparticles synthesized from *Balanites aegyptiaca* extract against lung carcinoma cells with $IC_{50}$=4.13 µl. Table 6 shows the cell viability and the inhibition percentage as a function of the sample concentration,

TABLE 6

| Sample | Viability % (3 Replicates) | | | | Inhibition | Standard Deviation |
|---|---|---|---|---|---|---|
| conc. (µl) | 1st | 2nd | 3rd | Mean | % | (±) |
| 100 | 7.42 | 5.96 | 6.14 | 6.51 | 93.49 | 0.80 |
| 50 | 15.7 | 12.81 | 13.29 | 13.93 | 86.07 | 1.55 |
| 25 | 22.32 | 20.44 | 21.93 | 21.56 | 78.44 | 0.99 |
| 12.5 | 26.31 | 27.97 | 30.62 | 28.30 | 71.70 | 2.17 |
| 6.25 | 38.93 | 40.62 | 41.28 | 40.28 | 59.72 | 1.21 |

TABLE 6-continued

| Sample | Viability % (3 Replicates) | | | | Inhibition | Standard Deviation |
|---|---|---|---|---|---|---|
| conc. (µl) | 1st | 2nd | 3rd | Mean | % | (±) |
| 3.125 | 54.72 | 56.08 | 52.97 | 54.59 | 45.41 | 1.56 |
| 0 | 100 | 100 | 100 | 100 | 0.00 | |

Figure 12:
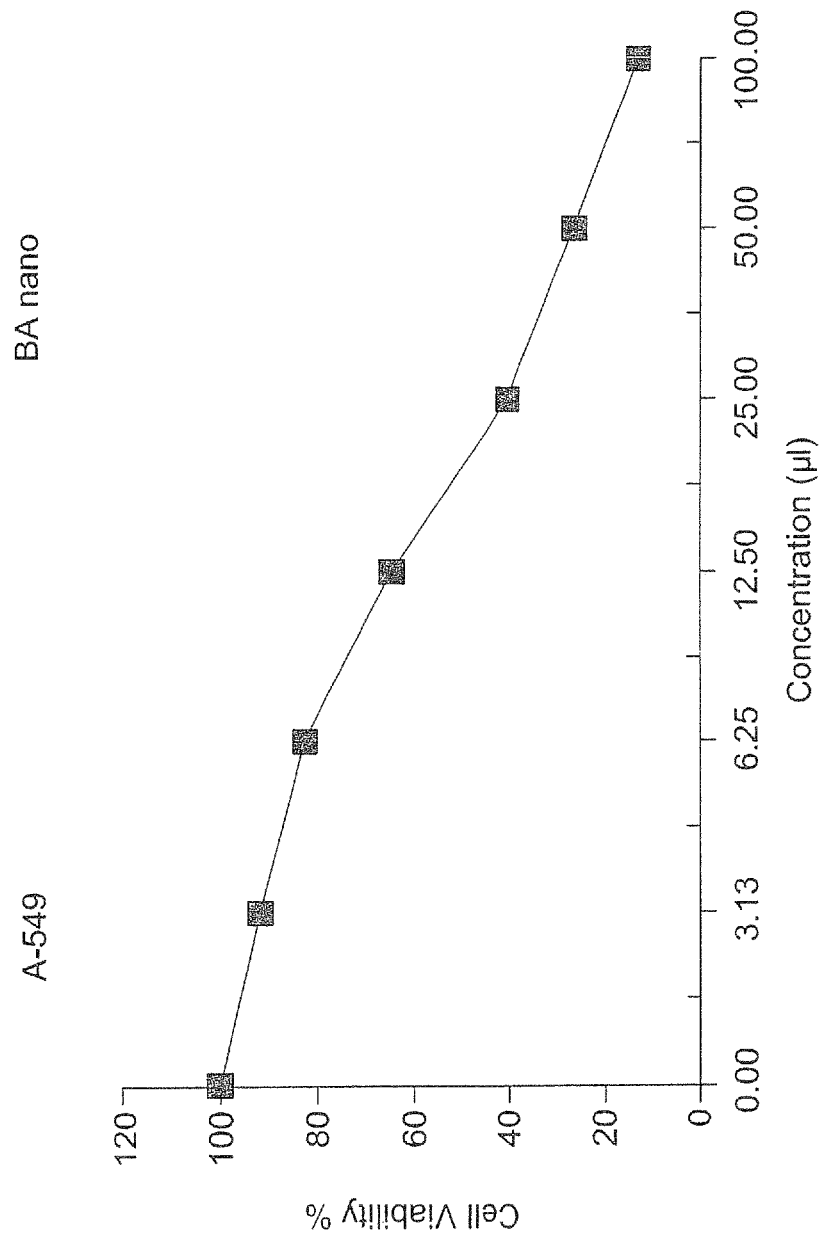
FIG. 12 is a graph showing the inhibitory activity of *Balanites aegyptiaca* nanoparticles against lung carcinoma cells.

FIG. 12 shows the inhibitory activity of *Balanites aegyptiaca* nanoparticles against lung carcinoma cells with $IC_{50}$=19.9 µl. Table 7 shows the cell viability and the inhibition percentage as a function of the concentration

TABLE 7

| Sample | Viability % (3 Replicates) | | | | Inhibition | Standard Deviation |
|---|---|---|---|---|---|---|
| conc. (µl) | 1st | $2^{nd}$ | 3rd | Mean | % | (±) |
| 100 | 14.78 | 10.92 | 13.64 | 13.11 | 86.89 | 1.98 |
| 50 | 27.24 | 24.89 | 26.71 | 26.28 | 73.72 | 1.23 |
| 25 | 39.74 | 42.56 | 38.19 | 40.16 | 59.84 | 2.22 |
| 12.5 | 68.95 | 63.27 | 60.54 | 64.25 | 35.75 | 4.29 |
| 6.25 | 87.29 | 80.94 | 78.85 | 82.36 | 17.64 | 4.40 |
| 3.125 | 94.13 | 91.86 | 89.27 | 91.75 | 8.25 | 2.43 |
| 0 | 100 | 100 | 100 | 100 | 0.00 | |

Example 6

Antimicrobial Screening Assay

Antimicrobial activity of nanoparticles was determined using the agar well diffusion assay method as described by Holder and Boyce, 1994. Three bacterial (two gram positive and one gram negative) and one yeast strain, namely, *Bacillis suhtilis* (RCMB 010067), *Staphylococcus pneumoniae* (RCMB 010011), *Escherichia coli* (RCMB 010052), and *Aspergillus fumigatus* (RCMB 02568). The tested organisms were sub-cultured on nutrient agar medium (Oxoid laboratories, UK) for bacteria and Sabouraud dextrose agar (Oxoid laboratories, UK) for fungi. Ampicillin and Gentamicin were used as positive control for gram positive and gram negative bacteria, respectively, while Amphotericin B was used for fungi. The plates were done in triplicates. Bacterial cultures were incubated at 37° C. for 24 h, while the fungal cultures were incubated at 25-30° C. for 3-7 days. Antimicrobial activity was determined by measuring the zone of inhibition [A. Agwa, (2000)]. The antimicrobial effect of the *B. aegyptiaca* nanoparticles was evaluated against different gram positive and gram negative bacteria as well as fungi. The results of the antimicrobial effects of the synthesized nanoparticles are compiled in the Tables below.

Table 8 represents the microorganism inhibition results using gold nanoparticles.

TABLE 8

| Sample/Tested microorganisms | Gold Nanoparticles | Reference Drug |
|---|---|---|
| FUNGI | | Amphotericin B |
| *Aspergillus fumigatus* (RCMB 02568) | 12.4 ± 0.58 | 23.7 ± 0.10 |
| *Geotricum candidum* (RCMB 05097) | NA | 28.7 ± 0.22 |

TABLE 8-continued

| Sample/Tested microorganisms | Gold Nanoparticles | Reference Drug |
|---|---|---|
| Grain Positive Bacteria: | | Ampicillin |
| Staphylococcus aureus (RCMB 010028) | NA | 27.4 ± 0.18 |
| Bacillis subtilis (RCMB 010067) | 15.9 ± 0.58 | 32.4 ± 0.10 |
| Gram negative Bacteria: | | Gentamicin |
| Pseudomonas aeruginosa (RCMB 010043) | NA | 17.3 ± 0.15 |
| Escherichia coli (RCMB 010052) | 15.9 ± 0.25 | 22.3 ± 0.18 |
| Shegella dysentriae (RCMB 010098) | 14.6 ± 0.44 | 17.3 ± 0.15 |
| Salmonella typhimurium (RCMB 010072) | 13.6 ± 0.58 | 25.4 ± 0.18 |
| Klebsiella pneumoniae (RCMB 000111) | 16.3 ± 0.25 | 20.2 ± 0.25 |

*Mean zone of inhibition in mm ± Standard deviation beyond well diameter (6 mm) produced on a range of environmental and clinically pathogenic microorganisms.
**The test was done using diffusion agar technique, Well diameter: 6.0 mm (100 µl) was tested, RCMB: Regional Center For Mycology And Biotechnology Antimicrobial unit test organisms
***NA: No activity, data are expressed in the form of mean ± SD.

Table 9 represents the microorganism inhibition results using zinc oxide (ZnO BA) nanoparticles and *Balanites aegyptiaca* (BA) nanoparticles.

TABLE 9

| Sample/Tested microorganisms | ZnO BA nanoparticles | BA nanoparticles | Standard |
|---|---|---|---|
| FUNGI | | | Amphotericin B |
| Aspergillus fumigatus (RCMB 02567) | 29.0 ± 1.0 | 22.0 ± 1.0 | 21.7 ± 1.5 |
| Gram Positive Bacteria: | | | Ampicillin |
| Streptococcus pneumoniae (RCMB 010011) | 29.3 ± 2.1 | 20.3 ± 2.5 | 21.0 ± 1.0 |
| Bacillis subtilis (RCMB 010068) | 33.3 ± 2.5 | 26.7 ± 1.5 | 31.3 ± 1.5 |
| Gram negative Bacteria: | | | Gentamicin |
| Escherichia coli (RCMB 010054) | 27.3 ± 2.5 | 24.3 ± 0.58 | 20.3 ± 0.58 |

Samples were tested at a concentration of 100 µl;
<sup>a</sup>Data are expressed in the form of (M ± S.D.): mean ± standard deviation; Diameter of the inhibition zone (mm) beyond the well diameter of 6 mm; NT: not tested; NA: no activity.

Thus, the above examples illustrate a non-toxic and environmentally friendly green synthesis of gold and zinc oxide nanoparticles using *Balanites aegyptiaca* mesocarp (desert dates) aqueous extract. The green synthesized gold and zinc oxide nanoparticles can have potential applications as antimicrobial and/or anti-cancer agents because these display enhanced in vitro activity as anticancer and antimicrobial agents.

It is to be understood that the present invention is not limited to the embodiments described above, but encompasses any and all embodiments within the scope of the following claims.

We claim:

1. A method of synthesizing nanoparticles containing a *Balanites aegyptiaca* (L.) extract, comprising the steps of:
   (a) preparing a *Balanites aegyptiaca* (L.) extract by soaking fruit powder of the *Balanites aegyptiaca* (L.) in water for about 12 hours and isolating the extract by centrifugation at about 5000 rpm, and
   (b) combining the extract of step (a) with a metal acid in aqueous solution at a temperature of about 70-90° C. to produce said nanoparticles,
   wherein the metal acid solution is selected from the group consisting of 0.001-0.005 mol/L chloroauric acid ($HAuCl_4$) and 0.05 mol/L of zinc nitrate hexahydrate ($Zn(NO_3)_2$, $6H_2O$).

2. The method according to claim 1, wherein the nanoparticles are spherical, spheroidal, elongated spherical, rod-shaped, and/or faceted.

* * * * *